United States Patent
Cankar et al.

(10) Patent No.: US 11,517,483 B2
(45) Date of Patent: Dec. 6, 2022

(54) METHOD OF FORMING PRIMARY PACKAGE TUBE FOR TAMPONS

(71) Applicant: Johnson & Johnson GmbH, Neuss (DE)

(72) Inventors: Thomas Cankar, Wuppertal (DE); Markus Klar, Wuppertal (DE); Markus Anger, Wuppertal (DE); Martin Bergermann, Wuppertal (DE); Jens-Petter Arnesen, Sezanne (FR)

(73) Assignee: Johnson & Johnson GmbH, Neuss (DE)

( * ) Notice: Subject to any disclaimer, the term of this patent is extended or adjusted under 35 U.S.C. 154(b) by 894 days.

(21) Appl. No.: 16/066,109

(22) PCT Filed: Dec. 30, 2016

(86) PCT No.: PCT/IB2016/058118
§ 371 (c)(1),
(2) Date: Jun. 26, 2018

(87) PCT Pub. No.: WO2017/115335
PCT Pub. Date: Jul. 6, 2017

(65) Prior Publication Data
US 2020/0146904 A1    May 14, 2020

Related U.S. Application Data

(60) Provisional application No. 62/273,775, filed on Dec. 31, 2015.

(51) Int. Cl.
*A61F 13/551* (2006.01)
*B65B 11/32* (2006.01)
(Continued)

(52) U.S. Cl.
CPC ........ *A61F 13/55175* (2013.01); *B65B 11/32* (2013.01); *B65B 19/00* (2013.01); *B65B 49/12* (2013.01)

(58) Field of Classification Search
CPC .... A61F 13/55175; A61F 13/20; B65B 11/32; B65B 19/00; B65B 49/12; B65B 5/02; B65B 47/06; B31B 50/64
(Continued)

(56) References Cited

U.S. PATENT DOCUMENTS 2,533,993 A    12/1950   Bryans
2,851,839 A    9/1958    Himes et al.
(Continued)

FOREIGN PATENT DOCUMENTS

EP    1010622 A    6/2000
EP    1010622 B    9/2003
(Continued)

OTHER PUBLICATIONS

International search report dated Mar. 23, 2017, for international application PCT/IB2016/058118.

*Primary Examiner* — Anna K Kinsaul
*Assistant Examiner* — Luis G Del Valle

(57) ABSTRACT

High-speed methods to close tubular plastic wrappers may include providing a packaging film on a mandrel in the form of a hollow tube, forming a folded surface by rotating the hollow tube and mandrel while counter-rotating a plate having a plurality of folding blades, to form a plurality of folds that define the folded surface, substantially perpendicular to the longitudinal axis of the hollow tube, each folding blade engaging a portion of the protruding tube portion, applying heat and pressure to the folded surface to form a closed end, inserting the tampon into the tube, and closing the first end of the tube. The film material comprises (Continued)

at least one thermoplastic surface, and the mandrel has a first end extending from a revolving platform and a second end, distal the first end. The mandrel can rotate with respect to the revolving platform on which it is mounted.

10 Claims, 5 Drawing Sheets

(51) Int. Cl.
*B65B 19/00* (2006.01)
*B65B 49/12* (2006.01)

(58) Field of Classification Search
USPC .......................... 53/575, 452, 456, 588, 563
See application file for complete search history.

(56) References Cited

U.S. PATENT DOCUMENTS

| | | | |
|---|---|---|---|
| 3,290,861 A | 12/1966 | Prager | |
| 3,468,412 A * | 9/1969 | Forman | B29C 66/73711 53/442 |
| 3,633,335 A | 1/1972 | Johnson | |
| 3,766,703 A | 10/1973 | Simon et al. | |
| 3,807,132 A | 4/1974 | Kamiya | |
| 3,856,143 A | 12/1974 | Simon et al. | |
| 3,924,375 A | 12/1975 | Brenner et al. | |
| 4,102,111 A * | 7/1978 | Nack | B65B 51/306 53/550 |
| 4,583,964 A | 4/1986 | Warncke | |
| 5,016,423 A | 5/1991 | Spatafora et al. | |
| 5,533,323 A * | 7/1996 | Osti | B29C 66/8227 53/375.9 |
| 5,907,941 A | 6/1999 | Fukuzumi et al. | |
| 5,987,847 A * | 11/1999 | Nordstrom | B65B 25/146 53/372.9 |
| 7,032,359 B1 | 4/2006 | Robert et al. | |
| 8,221,371 B2 | 7/2012 | Junio et al. | |
| 2003/0233813 A1 | 12/2003 | Leslie et al. | |
| 2010/0130954 A1* | 5/2010 | Handel | A61F 13/55175 206/440 |
| 2013/0168485 A1* | 7/2013 | Balzanelli | B65H 54/62 242/472.5 |
| 2019/0337648 A1* | 11/2019 | Heege | B65B 51/26 |

FOREIGN PATENT DOCUMENTS

| | | | | |
|---|---|---|---|---|
| EP | 1477406 A | 11/2004 | | |
| EP | 1477406 A1 * | 11/2004 | | B65B 11/32 |
| GB | 00921 A | 1/1916 | | |
| GB | 966121 A | 8/1964 | | |
| NL | 196917298 A | 5/1971 | | |
| WO | WO 2001/036272 A | 5/2001 | | |

* cited by examiner

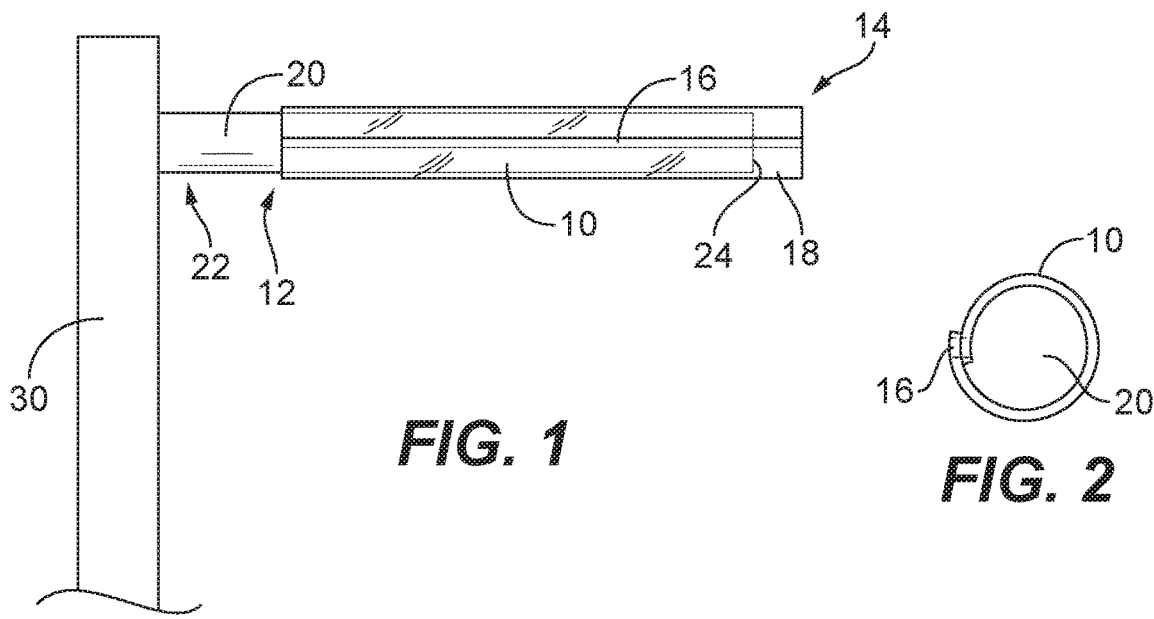
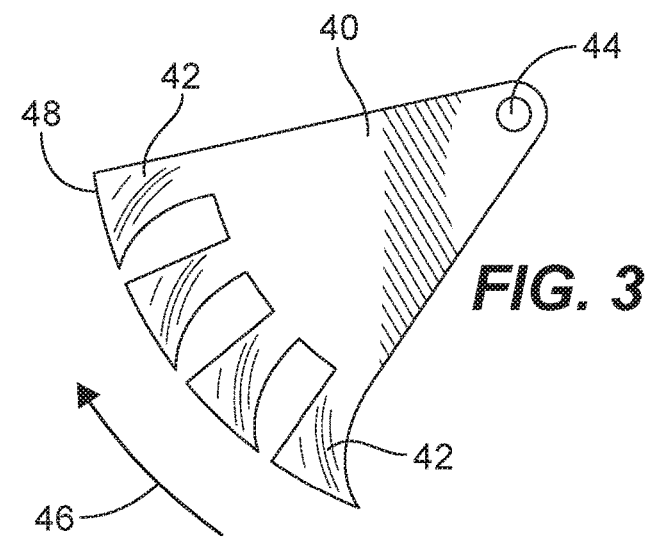
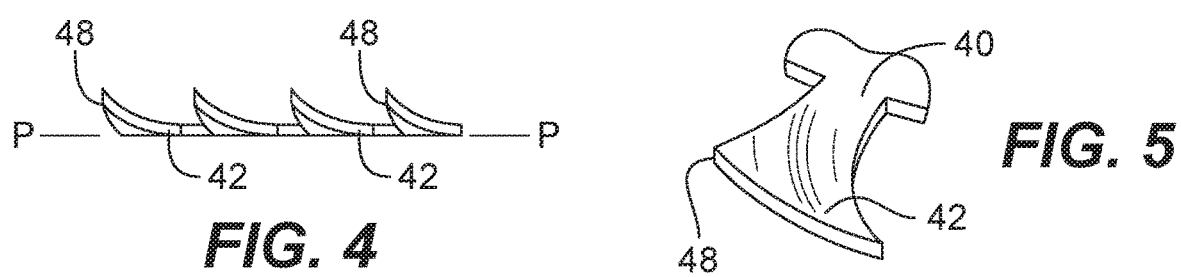

METHOD OF FORMING PRIMARY PACKAGE TUBE FOR TAMPONS

CROSS-REFERENCE TO RELATED APPLICATIONS

This application is the national phase filing under 35 USC 371 of international application PCT/IB2016/058118 filed Dec. 30, 2016, which claims the benefit of U.S. provisional application 62/273,775 filed on Dec. 31, 2015.

FIELD OF THE INVENTION

The present invention relates to a method of packaging a tampon.

BACKGROUND OF THE INVENTION

Methods for closing one end of tubular containers are known.

In view of the shortcomings of the prior art, what is needed is a high-speed method to close a tubular plastic wrapper for use with tampons.

SUMMARY OF THE INVENTION

The present invention relates to high-speed methods to close tubular plastic wrappers for use with tampons. In one embodiment, the process includes providing a packaging film on a mandrel in the form of a hollow tube, forming a folded surface by rotating the hollow tube and mandrel while counter-rotating a plate having a plurality of folding blades extending outwardly therefrom, to form a plurality of folds that define the folded surface, substantially perpendicular to the longitudinal axis of the hollow tube, each folding blade engaging a portion of the protruding tube portion, applying heat and pressure to the folded surface to form a closed end, inserting the tampon into the tube, and closing the first end of the tube. The packaging film material comprises at least one thermoplastic surface, and the mandrel has a first end extending from a revolving platform and a second end, distal the first end. In addition, the mandrel is capable of rotating with respect to the revolving platform on which it is mounted. In addition, the hollow tube has an overlapping longitudinal seam area having two plies of the packaging film and has a first end corresponding to the first end of the mandrel and a second end distal thereof, the second end extending beyond the second end of the mandrel to define a protruding tube portion, and a length extending from the first end to the second end; wherein the protruding tube portion has a length approximately equal to the radius of the hollow tube.

In an alternative embodiment, the folded surface is formed by rotating a plurality of folding blades perpendicular to the longitudinal axis of the hollow tube to engage the protruding tube portion to form a plurality of folds that define the folded surface, substantially perpendicular to the longitudinal axis of the hollow tube.

BRIEF DESCRIPTION OF THE DRAWINGS

FIG. 1 is a side elevation of an open wrapping tube disposed on a mandrel.

FIG. 2 is an end view of the open wrapping tube and mandrel of FIG. 1.

FIG. 3 is a plan view of a fan-like folding plate useful in the method of the present invention.

FIG. 4 is a side view of the fan-like folding plate of FIG. 3.

FIG. 5 is a perspective view of a folding blade of the folding plate of FIG. 3.

DETAILED DESCRIPTION OF THE INVENTION

Figure 6:
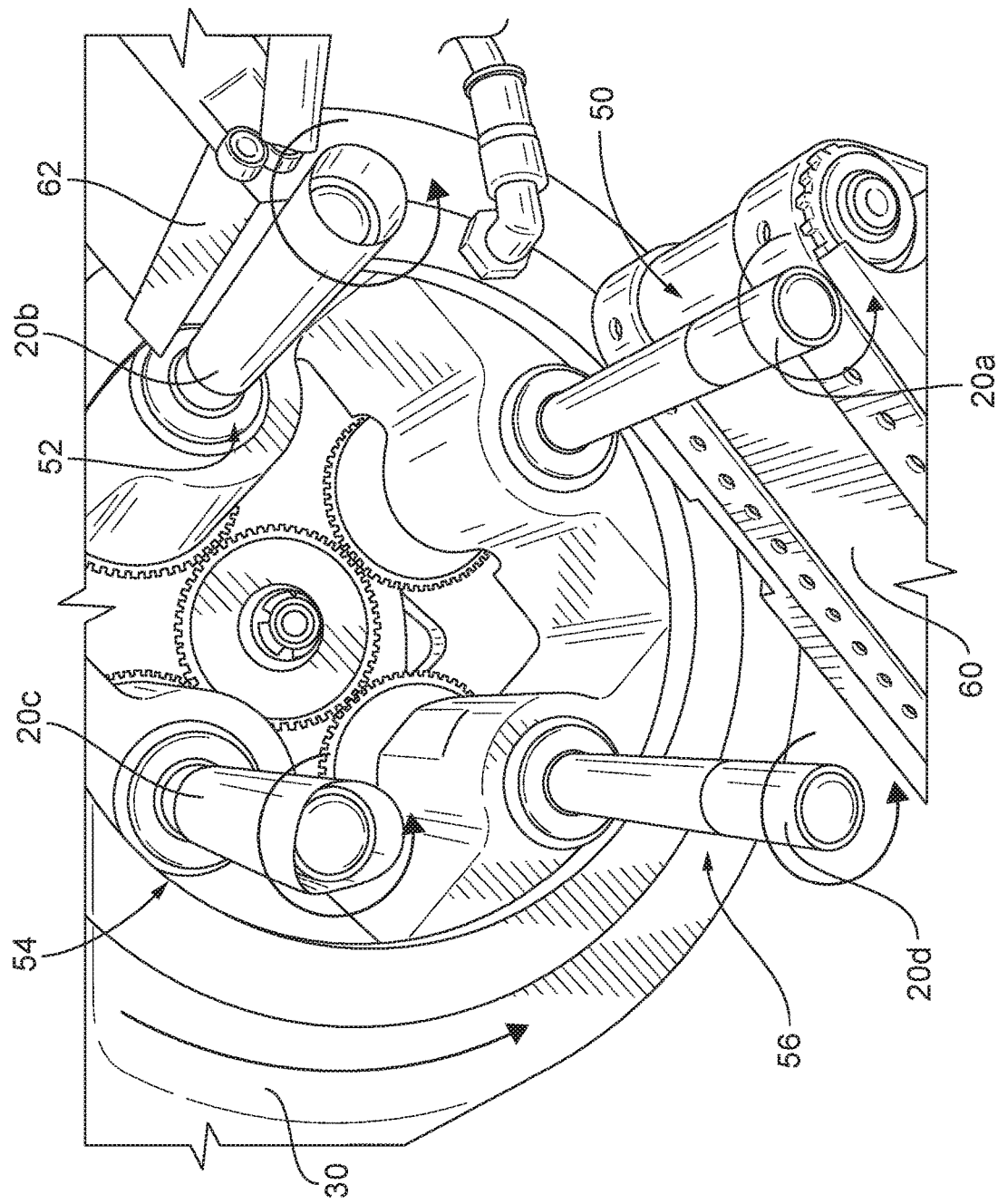
FIG. 6 is a perspective view of a revolver and ancillary equipment useful in the practice of the present invention.

The following is a detailed description of the present invention, wherein like elements are labeled with like numerals in FIGS. 1-11. Referring to FIGS. 1-2, a plastic wrapping film, formed into a flexible packaging tube 10 is disposed on a mandrel 20. The flexible packaging tube 10 has a first open end 12, a second open end 14 and a longitudinal seam 16. The mandrel 20 has a first end 22 extending from a revolving platform 30 and a second end 24, distal the first end 22, and a length extending from the first end 22 to the second end 24, and is capable of rotating with respect to the revolving platform 30. The second end 14 of the flexible packaging tube 10 extends beyond the second end 24 of the mandrel 20 to define a protruding tube portion 18.

FIGS. 3-5 show features of a fan-like folding plate 40 having four folding blades 42 that is rotatable about pivot 44 in the direction of arrow 46. When the folding plate 40 rotates in the direction of arrow 46, the leading edge 48 of each folding blade 42 is elevated with respect to the plane of the folding plate 40 to enable the folding blade 42 to engage the protruding portion 18 of the flexible packaging tube 10. The remainder of the folding blade 42 curves and/or slopes down to the plane "p-p" of the folding plate 40 (shown in FIG. 4). Thus, as each folding blade 42 moves across the protruding portion 18 flexible packaging tube 10, it forms a pleat across the open second end 24 of the flexible packaging tube 10. The four folding blades 42 of the embodiment of these figures would be capable of forming four pleats across the open end 24 of the flexible packaging tube 10. After these pleats are formed, they can be heated under pressure to soften the plastic wrapping film material to seal them in a manner to close the previously open second end 14 of the flexible packaging tube 10.

While four folding blades are shown in this embodiment, one of ordinary skill in the art will recognize that other numbers may be used, from three to eight or more. Preferably, the number of blades is between four and six.

FIG. 6 shows a revolving platform 30 having mounted thereon four mandrels 20. As shown in Position 50, a first mandrel 20a engages a conveyor 60 that delivers a supply of plastic wrapping film thereto. Each mandrel 20 can be equipped with apertures and/or slots to permit vacuum pressure to be drawn therethrough to hold the plastic wrapping film in place on the mandrel. As shown in Position 52, a second mandrel 20b is engaged with a longitudinal sealing bar 62 arranged and configured to seal overlapping plies of the plastic wrapping film to form the flexible packaging tube 10. Position 54 is the tube folding apparatus (not shown in this figure) and has a third mandrel 20c with a flexible packaging tube 10 ready for engagement with the tube folding apparatus. At Position 56, a fourth mandrel 20*d* has transferred the flexible packaging tube 10 for further processing.

Figure 7:
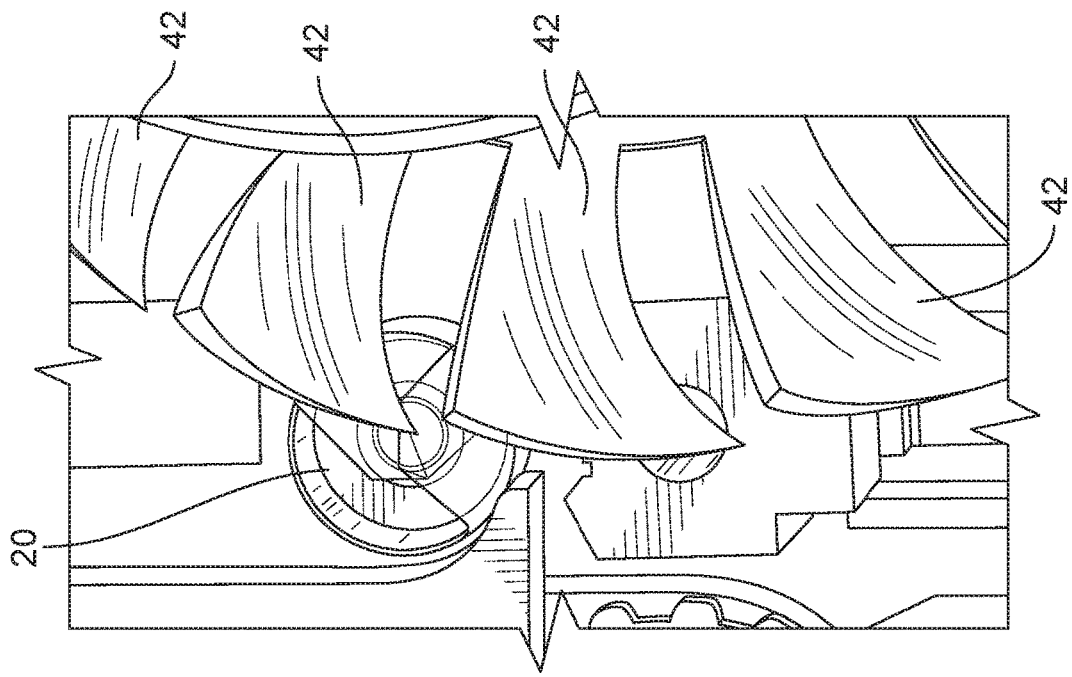
FIGS. 7 and 8 are close-up views of the engagement of the fan-like folding plate of FIG. 3 and the mandrel of FIG. 2 during the process of forming pleats across the second end of the wrapping tube of FIG. 2.
Figure 8:
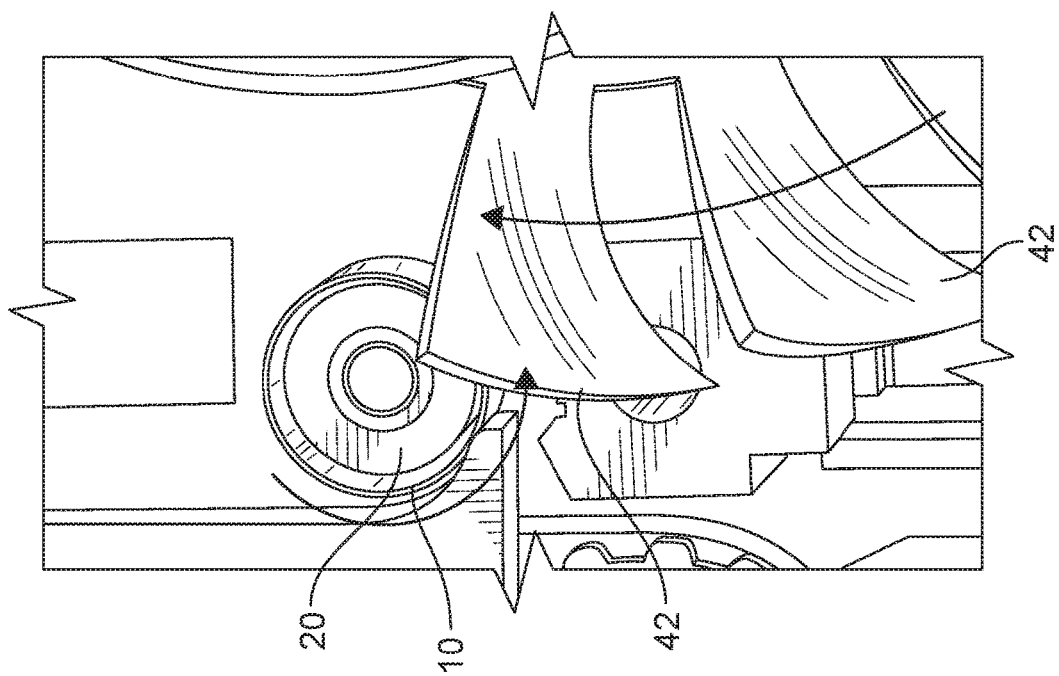

FIGS. 7 and 8 show the engagement of the folding blades 42 with the protruding portion 18 of the flexible packaging tube 10. As shown in FIG. 7, the mandrel 20 rotates in a counter-clockwise direction, while the folding blades 42 rotate in a clockwise direction. FIG. 8 shows the process partially completed with two of the folding blades 42 having made a corresponding number of folds across the second open end 14.

Figure 9:
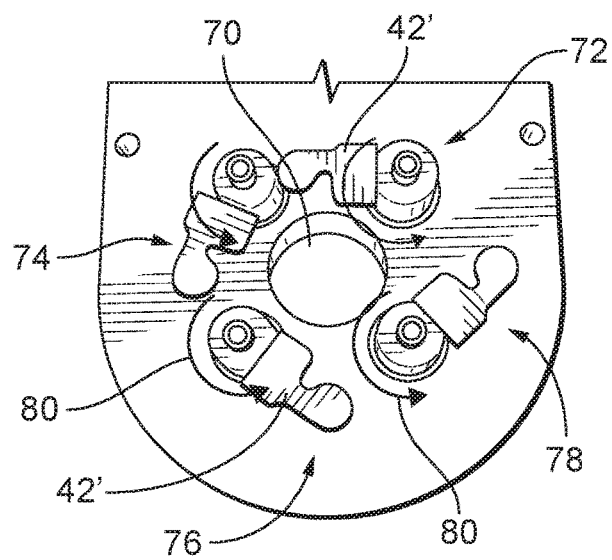
FIGS. 9-11 are plan views of an alternative embodiment of the wrapper tube closure apparatus of the present invention.
Figure 10:
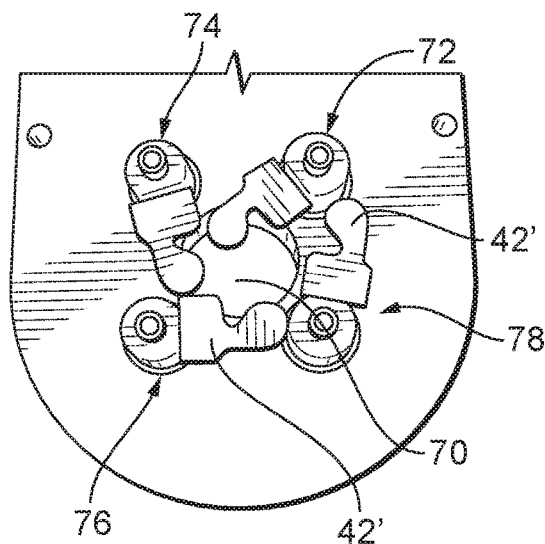
Figure 11:
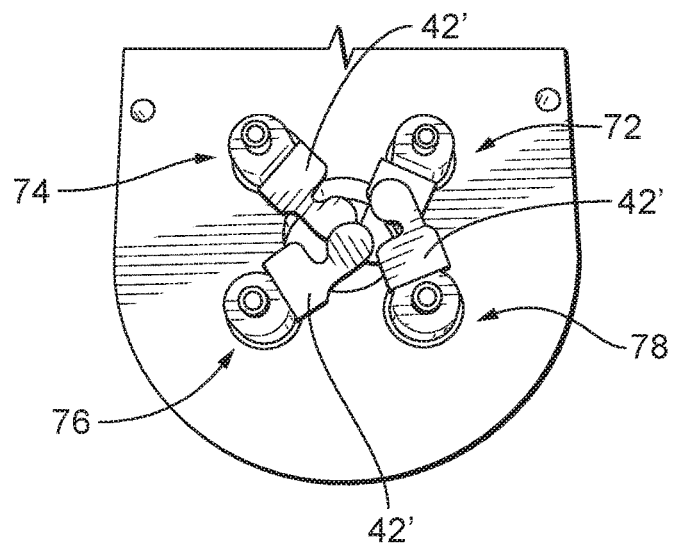
Figure 12:
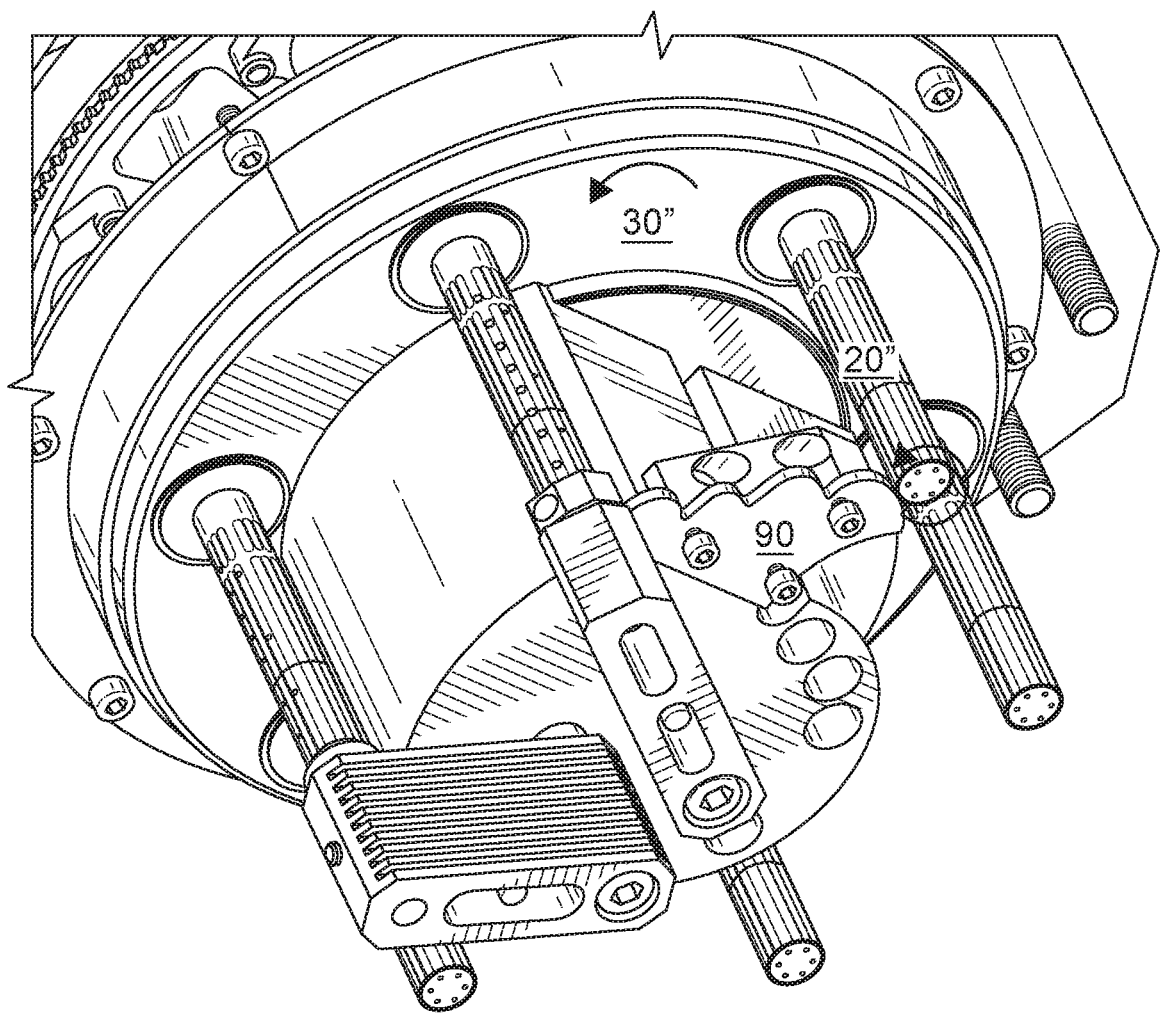

In an alternative embodiment, shown in FIGS. 9-11, the mandrel (not shown) remains stationary in aperture 70 while four independently rotatable folding blades 42' rotate, sequentially, e.g., starting at Position 72, followed by Position 74, Position 76, and Position 78. FIG. 9 shows the four independent folding blades 42' ready to fold in the direction of arrows 80. FIG. 10 shows the folding blades 42' corresponding to Positions 72 furthest across aperture 70 followed closely by Position 74, while the folding blade 42' corresponding to Position 76 approaches the aperture 70. FIG. 11 shows all four folding blades 42' disposed across aperture 70. After these pleats are formed, they can be heated under pressure to soften the plastic wrapping film material to seal them in a manner to close the previously open second end 14 of the flexible packaging tube 10.

While four folding blades are shown in this embodiment, one of ordinary skill in the art will recognize that other numbers may be used, from three to eight or more. Preferably, the number of blades is between four and six.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of packaging a tampon comprising the steps of:
    a) providing a packaging film on a mandrel in the form of a hollow tube, wherein:
        i) the packaging film material comprises at least one thermoplastic surface;
        ii) the mandrel has a first end extending from a revolving platform and a second end, distal the first end, and a length extending from the first end to the second end, and is capable of rotating with respect to the revolving platform,
        iii) the hollow tube of packaging film material has an overlapping longitudinal seam area having two plies of the packaging film and has a first end corresponding to the first end of the mandrel and a second end distal thereof, the second end extending beyond the second end of the mandrel to define a protruding tube portion, and a length extending from the first end to the second end; wherein the protruding tube portion has a length approximately equal to the radius of the hollow tube of packaging film material;
    b) forming a folded surface by rotating the hollow tube of packaging film material and mandrel with respect to the revolving platform while counter-rotating a plate having a plurality of folding blades extending outwardly therefrom, distal an axis of rotation thereof to form a plurality of folds that define the folded surface, substantially perpendicular to the longitudinal axis of the hollow tube of packaging film material, each folding blade engaging a portion of the protruding tube portion;
    c) applying heat and pressure to the folded surface to form a closed end of the hollow tube of packaging film material;
    d) inserting the tampon into the hollow tube of packaging film material; and
    e) closing the first end of the tube hollow tube of packaging film material.

2. The method of claim 1, wherein the packaging film comprises a thermoplastic film.

3. The method of claim 1, wherein the packaging film comprises a thermoplastic surface coating layer.

4. The method of claim 1, wherein the step of providing a packaging film on a mandrel in the form of a hollow tube comprises
    A) winding the packaging film around a tube-forming mandrel to form a hollow tube of packaging film material, and
    B) applying heat and pressure to the overlapping longitudinal seam area to form a longitudinal seam.

5. A method of packaging a tampon comprising the steps of:
    a) winding a packaging film around a mandrel to form a hollow tube of packaging film material, wherein:
        i) the packaging film material comprises at least one thermoplastic surface;
        ii) the mandrel has a first end extending from a revolving platform and a second end, distal the first end, and a length extending from the first end to the second end,
        iii) the hollow tube of packaging film material has an overlapping longitudinal seam area having two plies of the packaging film and has a first end corresponding to the first end of the mandrel and a second end distal thereof, the second end extending beyond the second end of the mandrel to define a protruding tube portion, and a length extending from the first end to the second end; wherein the protruding tube portion has a length approximately corresponding to the radius of the hollow tube of packaging film material;
    b) applying heat and pressure to the overlapping longitudinal seam area to form a longitudinal seam;
    c) forming a folded surface by rotating a plurality of folding blades perpendicular to the longitudinal axis of the hollow tube of packaging film material to engage the protruding tube portion to form a plurality of folds that define the folded surface, substantially perpendicular to the longitudinal axis of the hollow tube of packaging film material;
    d) applying heat and pressure to the folded surface to form a closed end of the hollow tube of packaging film material;
    e) inserting the tampon into the hollow tube of packaging film material; and
    f) closing the first end of the tube hollow tube of packaging film material.

6. The method of claim 5, wherein the packaging film comprises a thermoplastic film.

7. The method of claim 5, wherein the packaging film comprises a thermoplastic surface coating layer.

8. The method of claim 1 wherein the plate defines a plane perpendicular to its axis of rotation and each folding blade comprises a leading edge that is elevated with respect to the plane defined by the plate.

9. The method of claim 5 wherein the mandrel is capable of rotating with respect to the revolving platform and wherein the folded surface is formed rotating the hollow tube and mandrel with respect to the revolving platform while counter-rotating a plate comprising the plurality of folding blades.

10. The method of claim 9 wherein the plate defines a plane perpendicular to its axis of rotation and each folding blade comprises a leading edge that is elevated with respect to the plane defined by the plate.

\* \* \* \* \*